Figure 1:
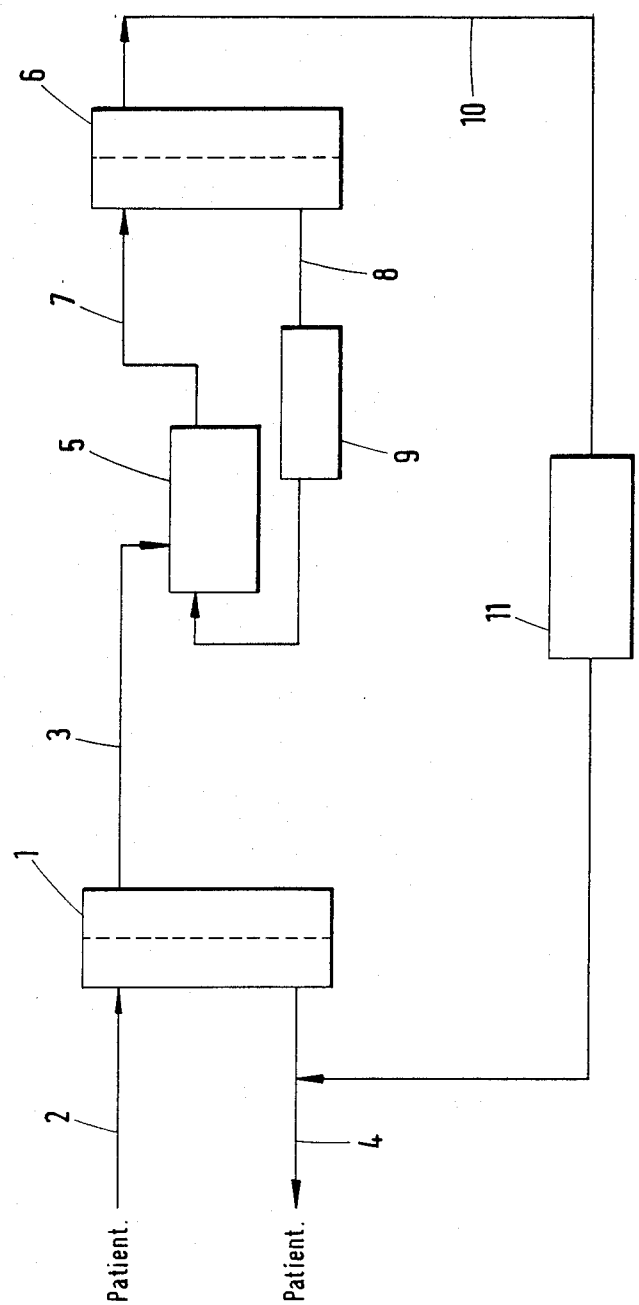

United States Patent [19]

Jorstad et al.

[11] Patent Number: 4,872,978
[45] Date of Patent: Oct. 10, 1989

[54] DEVICE FOR THE REMOVAL OF CRYOGLOBULINS

[75] Inventors: Storker Jorstad, Trondhjem, Norway; Leif Smedby, Lund, Sweden

[73] Assignee: Fabio Fasting Biotech A/S, Trondhjem, Norway

[21] Appl. No.: 125,419

[22] Filed: Nov. 25, 1987

[30] Foreign Application Priority Data

Nov. 26, 1986 [NO] Norway ................................ 864728

[51] Int. Cl.⁴ ...................... B01D 35/18; B01D 36/02; B01D 36/04
[52] U.S. Cl. .................................... 210/181; 210/182; 210/195.2; 210/195.3; 210/257.2; 210/259; 210/314; 210/321.6; 210/905
[58] Field of Search ........................... 604/4, 5, 6, 410; 210/175, 181, 182, 194, 195.1, 195.2, 252, 257.1, 257.2, 258, 259, 295, 321.72, 321.6, 905, 314; 530/380, 383, 830

[56] References Cited

U.S. PATENT DOCUMENTS 3,986,506 10/1976 Garber et al. .................. 604/410
4,350,156 9/1982 Malchesky et al. ............. 210/434

FOREIGN PATENT DOCUMENTS 0041350 12/1981 European Pat. Off. .

OTHER PUBLICATIONS

Plasauto TM 1000, "Asahi Plasma Treatment System", Asashi Medical Co., Ltd.
Cryomax® "Cryofiltration and Plasma Exchange", Parker Biomedical.

Primary Examiner—W. Gary Jones
Attorney, Agent, or Firm—Fleit, Jacobson, Cohn, Price, Holman & Stern

[57] ABSTRACT

An apparatus for cryoprecipitation of blood plasma, where the blood from a patient is fed to a plasma separator (1) in order to obtain blood plasma which is then cooled to about +4 degrees centigrade. The blood plasma from the plasma separator is next fed into a container (5). As the contents of the container are kept at a sufficiently low temperature, cryoprecipitation occurs in the container. The blood plasma from the container is then circulated preferably in a loop past a plasma filter (60), where a cooling unit (9) is placed on a branch of the loop (7,8). The filtrate from the plasma filter (6) is finally returned to the patient after it has been warmed in a heating unit (11).

14 Claims, 2 Drawing Sheets

DEVICE FOR THE REMOVAL OF CRYOGLOBULINS

The present invention concerns a device for the cryoprecipitation of blood plasma, where blood from a mammal including humans is led to a plasma separator to separate the blood cells from the blood plasma. The plasma is led from the plasma separator through tubes to a plasma filter (dialysis filter). The filtrate from the plasma filter is led to a heating unit which can warm the filtrate before it is returned to the heat.

Certain individuals suffer from the pathological condition where blood precipitates in their veins and blood vessels when their body temperature sinks below a normal level, caused by factors such as lying close to an open window in chilly weather. Such proteins are called cryoglobulins. This type of precipitation can result in instantaneous pathogenic conditions, such as disturbed blood circulation and attacks on the blood cells that have been affected. Precipitation can also lead to macromolecular aggregates that act as immune complexes. An immune complex consist of binding one or many antigens to one or more antibodies. These complexes can result in chronic cases of illness if they attack internal organs, connecting tissue and joints.

Previously, cryoprecipitation has been performed by removing cryoglobulins continually from the blood of a patient. This can be done by temporarily removing plasma from the blood cells and cooling it to about +4 degrees centigrade. At this temperature all types of pathological cryoglobulins will precipitate and can be removed from the blood stream with suitable equipment. The cleansed plasma is then warmed to body temperature and can be returned to the patient.

An apparatus for this purpose is already on the market, "Cryomax" from Parker Hannifin Corporation. This apparatus leads the blood through a plasma separator with a filter that separates the blood cells from the plasma which is allowed through the filter. The plasma is then cooled and led to a porous filter which is permeable for vital substances such as albumin and nutrients, whilst the harmful substance that have been precipitated by the cooling are retained in the preceding part of the apparatus. The plasma compounds which are allowed through the filter are then warmed before being fed into the bloodstream containing blood cells from the plasma separator and then back to the patient.

The considerable drawback with this apparatus is that the pores in the filter for the cooled cryoprecipitated gradually become clotted. This causes an increase in the pressure upon the filter and the transport of fluids and important substances will be reduced and finally halted. Consequently it is necessary to change the filter once or more during the course of a treatment.

This apparatus can also be criticised because of the bulkiness of its cooling system and its unnecessarily high cost.

The purpose of the present invention is therefore to devise a means of cryoprecipitation which permits longer periods of operation without a change of filter, preferably one that permits a larger filtration capacity without the risk of clotting.

A further objective is reducing the special requirements and the price of such an apparatus. A specific objective with the present invention is designing an apparatus where the plasma filter that is to remove the cryoglobulins from the remaining plasma compounds cannot be clogged by cryoglobulins, i.e., the tendency towards clotting in the pores is reduced.

These objectives are realized by a device which has been defined in the introduction where the plasma filter is incorporated in a recirculation circuit where the plasma is led through a cooling element and a container back to the plasma filter. The plasma from the plasma separator is fed into the container.

It is important that when this apparatus is operating that the plasma reaches the plasma filter with sufficient velocity to ensure that the pores are flushed. This flushing will prevent the pores from becoming clotted. The plasma filter is constructed of thin parallel tubes which the separated blood plasma and recirculating plasma flow through, whilst the lower molecular components diffuse through the walls of the tubes which have a measured pore-size with a cut-off larger or equal to $10^5$ daltons. This will result in the albumin and other smaller molocules going through the walls of the tubes in the plasma filter and are removed from there as a filtrate, whilst the cryoglobulins which form larger aggregates following cooling are flushed through the tubes in the filter and are returned through the cooling element to the container where this recirculating plasma is mixed with the filtrate from the plasma separator. The result is a residue fluid stream which is the multiple of the fluid flow from the plasma separator per unit of time.

A Peltier element would be an ideal cooling device for the recirculation circuit since it is both extremely compact and produces efficient cooling.

The container where the filtrate from the plasma separator and the recirculating plasma from the plasma filter are mixed should have a high vertical sides with a bottom outlet for tapping.

It is important that the container is adequately designed for the incoming streams so that strong turbulence is avoided and the cryoprecipitants can deposit sediments which remain largely undisturbed by the outlet stream to the plasma filter.

This can be achieved by leading the recirculating plasma stream which comes from the cooler into the middle of the container, preferably into the lower third of the upper half of the container.

The stream from the plasma separator on the other hand can be fed into the container lower down, preferably in the bottom quarter, thus rising against the flow of the precipitants which are depositing sediments in the container. The outlet for the plasma filter should preferably be located in the upper quarter of the container.

A suitable material for the container would be plastic and it could consequently be shaped like a plastic bag.

The container can either be closed or there can be a filter at the top to prevent the entry of contaminants from the environment surrounding the container.

A satisfactory design for the tap could be a valve which is activated by microprocessors when a specified pressure level is reached in the dialysis filter since the pores will become clotted after extended use and the pressure will consequently increase.

The plasma filter can be regenerated by back washing the pores with saline water or a solution of a protein such as albumin, thus declogging the pores.

Figure 2:
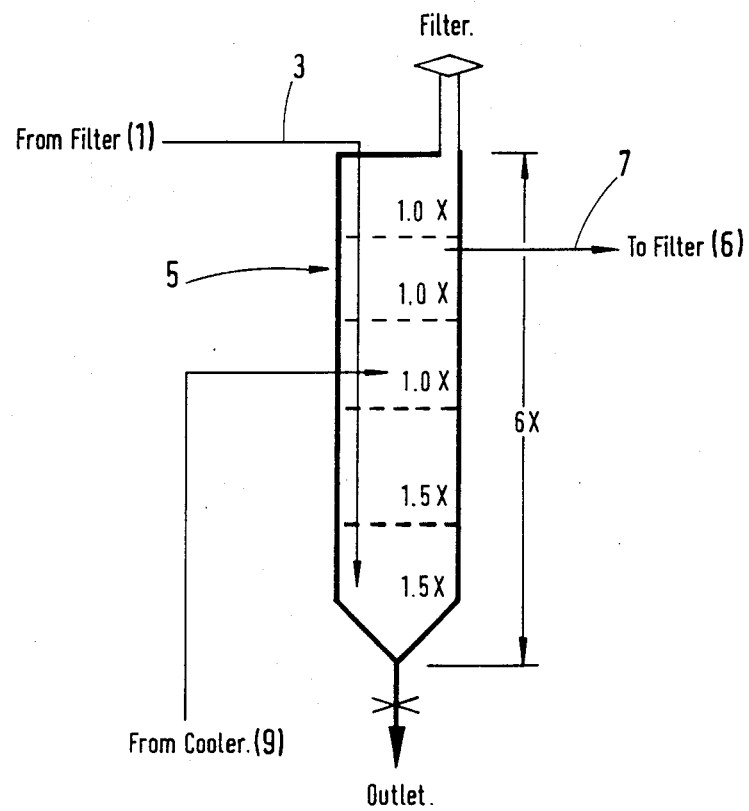

The invention will be described in more detail with reference to the enclosed figures where:

FIG. 1 gives a schematic representation of the complete cryoprecipitation apparatus designed in accordance with the invention, and FIG. 2 is a schematic representation of the container mentioned above.

In FIG. 1 a plasma separator 1 is shown which is an existing type of filter to separate blood cells from plasma. This filter operates best with a nominal cut-off larger that $10^6$ daltons.

Blood is led through a tube 2 into the plasma separator, the plasma which is free of blood cells is removed through tube 3, whilst the blood cells that cannot escape through the separator are led back to the patient through tube 4.

The plasma is then led through tube 3 to a container 5. This container 5 forms part of a circulation circuit where the outlet from the container 5 is led through tube 7 to a plasma filter (dialysis filter) 6, and the retained plasma is led by a return tube 8 through a cooling element 9 back to the already-mentioned container 5. The circulation in the circuit comes by means of a pump (not illustrated), preferably located between the plasma filter 6 and the cooling element 9.

The cooling element could also be placed in tube 7. This cooling element is preferably comprised of one or more Peltier elements which transfer the thermal energy from the plasma flow to the surrounding flowing coolant, air or water for instance. The cooling element 9 is designed so that the temperature of the plasma in the container 5 can be maintained close to +4 degrees centigrade.

The filtrate from the plasma filter 6 is pumped by non-illustrated pumps through a filtrate tube 10 to a heating unit 11 which warms the cleansed plasma up to body temperature before it is fed into tube 4 containing the blood cells from the plasma separator 1, and can then be led to the patient.

Since the fluid mixture in the container 5, as mentioned previously, will normally be at a temperature close to +4 degrees centigrade, the cryglobulins will mainly precipitate in the container. This temperature could in fact be set at anything between +4 and 37 degrees centigrade for cryoglobulins that do not require such a low temperature to start precipitation. With these sediments in the container, the load on the plasma filter 6 will be reduced and thereby the amount of cryoglobulins which are deposited on the pores of the plasma filter 6. This produces the desired reduction in pore clotting and a considerable reduction in the disruption frequency during plasma filtration in relation to methods known today. Hence the filter can be used much longer before replacement or cleaning than is the case with the filters used with existing equipment today. The container shown in FIG. 2 is supplied with filtrate from the plasma separator in the lower quarter of the container, whilst the recirculating plasma from the plasma filter is led into the lower third of the upper half of the container. The outlet from the container 5 is located higher than the two inlets to reduce the amount of cryoglobulins being carried along in the circulation. There is a filter to prevent contamination from the surrounding air on the top of the container. As indicated previously, the cryoglobulins will deposit sediment on the bottom of the container 5, however since a certain amount of turbulence is unavoidable some cryoprecipitates, will be transported into circulation through tube 7. In the bottom of the container there is a tap which is operated through a non-illustrated micro-processor which is activated in connection with a pressure build-up in the plasma filter 6, e.g., to 300 mm. Hg.

There can also be a degree of precipitation of cryoglobulins in tube 7. These, like the cryoglobulins that come from the container, may contribute to clotting the membrane pores in the plasma filter 6. Pressure registrations can be continuous or periodic. When an upper specified limit is reached, as will be the case if a patient has large quantities of these cryoglobulins in his or her blood stream, the boundary value set for pressure on the plasma filter will give a message to the pumping system to cease filtration above the filter. This will reduce the pressure above the membrane to roughly atmospheric values, the same pressure as in the container 5. This will remove the substances that have been pumped into the pores of the membrane. Once the pump that carries the fluid in tubes 7 and 8 stops, the pressure will rapidly fall towards atmospheric pressure. At the same time, a valve in the botton of the container 5 will open to allow some plasma to be tapped, for instance about 100 ml. with a high concentration of cryoprecipitate. This should be done within a given period of time, preferably under approximately one minute.

The apparatus could be further simplified by designing the cooling element 9 together with the heating element 11 so that the thermal energy is transferred to the latter. If the cooling element 9 was located downstream from the plasma filter 6, this has the advantage that the recirculating plasma from the plasma filter 6 will be returned to the container 5 at the lowest possible temperature.

The supply of blood plasma through tube 3 is controlled so that the container does not contain more than a specified volume. The supply will consequently be halted when the micropores in the plasma filter 6 become blocked and the cryoprecipitate has to be tapped from the container 5.

We claim:

1. A device for the cryoprecipitation of blood plasma, said device comprising:
   a plasma separator for the separation of blood cells from blood plasma in blood from a mammal,
   a sedimentation container,
   a first tube connecting said plasma separator and said sedimentation container,
   a plasma filter,
   a second tube connecting said plasma filter and said sedimentation container, for the supply of blood plasma from said plasma separator to said plasma filter,
   an outlet tube from said plasma filter for flow of filtrate from said plasma filter for return to a host,
   a heating device for the filtrate flowing through said outlet tube,
   a recirculation tube connected to said plasma filter and said sedimentation container for recirculating plasma from said plasma filter back to said plasma filter through said sedimentation container and said second tube,
   a cooling device for said recirculation tube for cooling the recirculating plasma between said plasma filter and said sedimentation container.

2. A device in accordance with claim 1, wherein said cooling device is a thermoelectric cooling system.

3. A device in accordance with claim 1, wherein said sedimentation container has a tapping arrangement.

4. A device in accordance with claim 1, wherein a tapping orifice is located at a bottom of said sedimentation container.

5. A device in accordance with claim 1, wherein said recirculation tube enters said sedimentation container above its vertical midpoint.

6. A device in accordance with claim 1, wherein said first tube from said plasma separator enters a lower quarter of said sedimentation container.

7. A device in accordance with claim 1, wherein said sedimentation container is made of plastic.

8. A device in accordance with claim 1, wherein said sedimentation container is a plastic bag.

9. Device for cryoprecipitation of blood plasma, said device comprising:
- a plasma separator for separating blood corpuscles from blood plasma in blood from a mammal,
- a plasma filter,
- tubes for supply of blood plasma from said plasma separator to said plasma filter,
- a discharge tube from said plasma filter, said discharge tube having a heating means for filtrate to be returned to the blood source,
- means for recirculation of the retentate from said plasma filter, said means including a recirculation tube for recirculating the retentate from the plasma filter and cooling means for cooling the retentate, said recirculating tube leading to a sedimentation container provided in a path of said tubes between said plasma separator and said plasma filter.

10. The device of claim 9, wherein said cooling means is provided in said recirculation tube.

11. The device of claim 9, wherein pump means are provided in said means for recirculation for activating a stream of liquid to reduce clogging of said plasma filter.

12. The device of claim 9, wherein said cooling means is a thermoelectric cooling system.

13. The device of claim 9, wherein said sedimentation container has a discharge opening in its bottom.

14. The device of claim 9, wherein said sedimentation container is a plastic bag.

* * * * *